United States Patent [19]

Hösel

[11] Patent Number: 4,903,374
[45] Date of Patent: Feb. 27, 1990

[54] APPARATUS FOR DETERMINING QUANTITIES OF FIBER CONVEYED THROUGH A DUCT

[75] Inventor: Fritz Hösel, Mönchengladbach, Fed. Rep. of Germany

[73] Assignee: Trutzschler GmbH & Co. KG, Mönchengladbach, Fed. Rep. of Germany

[21] Appl. No.: 331,371

[22] Filed: Mar. 31, 1989

[30] Foreign Application Priority Data

Apr. 2, 1988 [DE] Fed. Rep. of Germany ....... 3811332

[51] Int. Cl.$^4$ ............................................... D01B 7/00
[52] U.S. Cl. ..................................... 19/80 R; 19/97.5
[58] Field of Search ...................... 19/80 R, 97.5, 105, 19/240, 241, 300

[56] References Cited

U.S. PATENT DOCUMENTS 4,785,504 11/1988 Leifeld et al. ...................... 19/80 R
4,839,943 6/1989 Leifeld ................................. 19/80 R

FOREIGN PATENT DOCUMENTS 1401082 6/1988 U.S.S.R. ................................ 19/300

Primary Examiner—Werner H. Schroeder
Assistant Examiner—D. Price
Attorney, Agent, or Firm—Spencer & Frank

[57] ABSTRACT

An apparatus which determines quantities of textile fiber material during conveyance thereof by an air stream through a duct, includes a sensor unit situated at the duct and arranged for monitoring the stream flowing through the duct and composed of a fiber/air mixture. The sensor unit comprises a plurality of side-by-side situated light emitters forming an emitter bank and a plurality of side-by-side arranged light detectors forming a detector bank. The detector bank is situated spaced from and opposite to the emitter bank for providing a passage for the stream therebetween.

16 Claims, 6 Drawing Sheets

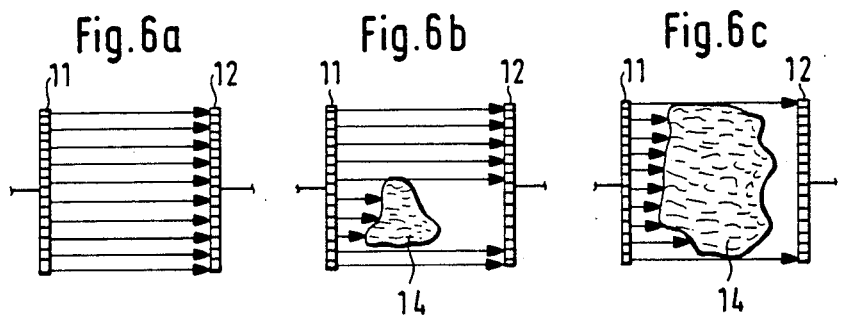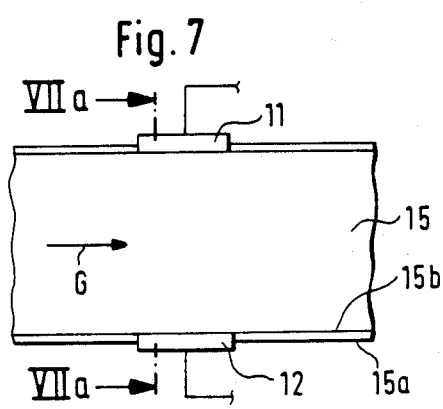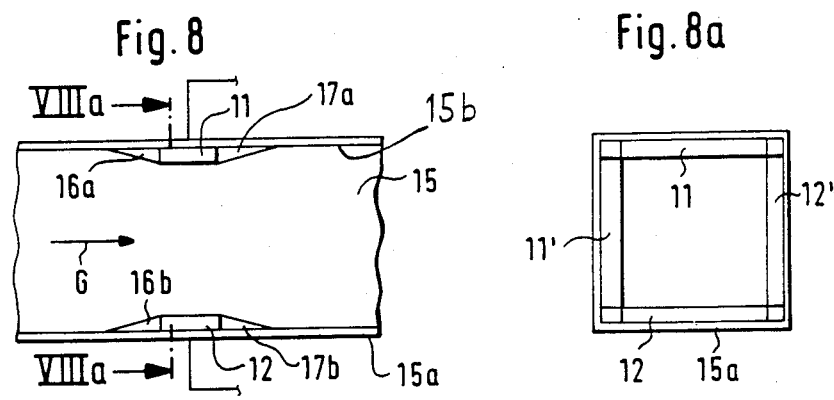

4,903,374

APPARATUS FOR DETERMINING QUANTITIES OF FIBER CONVEYED THROUGH A DUCT

CROSS REFERENCE TO RELATED APPLICATION

This application claims the priority of Federal Republic of Germany Application No. P 38 11 332.5 filed Apr. 2nd, 1988, which is incorporated herein by reference.

BACKGROUND OF THE INVENTION

This invention relates to an apparatus in the field of spinning preparation and is more particularly concerned with determining the quantities of fiber such as cotton, chemical fibers or the like pneumatically conveyed through a duct with flow rate control. The apparatus includes a sensor unit which monitors the advancing fiber stream.

In fiber processing machines which serve for the spinning preparation of fiber, the momentary fiber quantity actually being conveyed has to be determined particularly in case the rate of fiber feed is to be regulated. In order to be able, for example, to adapt the feed of a bale opener to the fiber material requirement of the subsequent fiber processing machines of a fiber processing line, it has to be determined how much fiber material the bale opener produces at any given moment.

A known apparatus comprises an optical barrier assembly which functions as a sensor for setting the fiber removal height of the detaching device of a bale opener. The optical barrier assembly is formed of a light emitter and a photocell (such as a selenium cell) responding to the incident light. The emitter and receiver are connected by means of control conductors with a switching device, for example, a switching relay station. The optical barrier assembly is mounted on the outlet duct for the fiber detached from the fiber bales. It is feasible to provide a plurality of light emitters and light detectors, whose switching relays are each set to a predetermined density of the fiber stream. In such an arrangement where a predetermined switching relay is set to respond to a predetermined quantity throughput, there is effected, by means of the relay, an upward or downward motion of the fiber detaching device (for example, one or more sawtooth rollers), together with the housing in which the detaching device is accommodated. In this manner there is ensured a constant fiber flow rate during the fiber bale opening process. If an optical barrier device is used which has a single light emitter and a single detector, all that can be determined is whether or not fiber material passes between the emitter and the receiver. The actual quantity of the fiber material throughput thus cannot be ascertained. In case a plurality of emitters and receivers is used with the associated separate switching relays, a determination of the actual throughput quantity is also not possible, because at each time only stepwise one or the other emitter/receiver pair is connected to the associated relay. Since a constant fiber stream is being produced, a regulation as a function of a variable fiber stream, particularly as a function of the quantity requirements by the after-connected fiber processing machines is not possible with prior art arrangements discussed above.

SUMMARY OF THE INVENTION

It is an object of the invention to provide an improved apparatus of the above-outlined type, from which the discussed disadvantages are eliminated and which, in particular, makes possible in a simple manner an exact determination (measurement) of the conveyed fiber quantities.

This object and others to become apparent as the specification progresses, are accomplished by the invention, according to which, briefly stated, the sensor unit of the quantity determining apparatus comprises a light emitter bank formed of a plurality of serially arranged light senders and a receiver bank formed of a plurality of light detectors. The emitter bank and the receiver bank are located opposite one another to allow the fiber material to pass therebetween.

The light emitters send light rays to the light receivers. By virtue of the plurality of light emitters and light receivers (light emitter bank and light receiver bank) there is obtained a shadow effect which reproduces the conveyed fiber tufts on the light receiver bank. The number of light receivers on which no light impinges at any given time is a measure of the fiber quantity of the fiber quantity momentarily present between the emitter bank and the receiver bank. This arrangement permits an exact measurement of the fiber material stream, that is, the arrangement makes possible to determine the dimension of the fiber tufts or the coherent fiber clusters.

Advantageously, the sensor unit is arranged in a conveyor duct of rectangular or square cross section. For this purpose, for example, a duct portion of rectangular cross section may be inserted in the fiber conveying conduit which has an otherwise circular cross section. Advantageously, the light emitter bank and the light receiver bank each are flush with the inner wall of the conveyor duct and thus form a contiguous part thereof, to ensure that flow-dynamically the fiber material remains undisturbed and thus may slide without impediment along the inner wall of the duct. In a preferred alternative, the light emitter bank and the light receiver bank are situated on the inner wall of the conveyor duct and the banks are provided, at least at their upstream portions (as viewed in the direction of fiber advance) with fiber tuft guide elements. Such an arrangement is particularly adapted for retrofitting a conveyor duct and ensuring, nevertheless an undisturbed fiber flow.

The apparatus according to the invention is expediently combined with a fiber bale opener which has a fiber detaching device, such as rotary toothed rollers which travel over the serially arranged fiber bales and whose height is adjusted for each pass. The fiber tufts torn from the upper face of the fiber bales by the detaching device are removed from the zone of the detachers by an air stream and introduced into a pneumatic conveyor duct. The fiber material quantities to be removed from the bales by the detacher are controlled by the sensor unit constructed according to the invention. The detacher is held in a housing cantilevered to a travelling turret propelled back and forth along the fiber bales. Advantageously, the sensor unit according to the invention is arranged in the stationary suction channel which extends horizontally underneath the bale opener turret along its path of travel. The cross-sectional area of the stationary channel is relatively large and rectangular, both characteristics favoring the installation of the sensor unit therein. It is of further advantage that the stationary suction channel is situated in a close vicinity to the bale opener permitting short electric connections, for example, to the driving arrangements.

In the alternative, the sensor unit according to the invention may be situated in the vertical suction duct situated inside the turret and is thus located between the detacher and the stationary suction channel. Or, the sensor unit may be situated in a duct portion which adjoins the stationary channel downstream thereof as viewed in the direction of fiber material advance. According to another alternative, the sensor unit is situated at the upstream end of the vertical duct portion, in the vicinity of the fiber detaching device.

According to a further feature of the invention, there are provided two light emitter banks and two light detector banks which are arranged pairwise, in a 90° offset relative to one another so that they form a rectangular outline in which the light beams of the emitters of one pair are perpendicular to the light beams of the emitters of the other pair. By detecting light beams simultaneously from two directions, the accuracy of the measurement can be further increased.

According to further features of the invention, a plurality of light sensor units according to the invention may be arranged in series parallel to the direction of fiber advance. While visible light may be used, it is particularly advantageous to use infrared light emitter and receiving devices in which detection errors normally caused by external light interferences (daylight) are significantly reduced. Preferably, pulsating infrared light is utilized.

According to a further feature of the invention, the light emitters and the light receivers are connected to a common electronic evaluating and control device. The information derived from the individual receivers of the receiver bank supplies a total image of the fiber quantity, since the individual receivers work simultaneously, in cooperation with one another.

The electronic evaluating circuit can count the number of the "dark" light receivers, add the count and form a mean value. Such a value may be modified by empirical values by providing it with a factor or may be calculated, for example, by integration. Influencing magnitude as correcting values may be the air speed, the type of material (cotton, polyester, cellulose fiber, etc.), air quantity and suction output.

According to a further advantageous feature of the invention the light emitters and receivers are coupled to an emitter and detector control device which, in turn, is connected to an electronic microcomputer control. The latter is coupled with the regulatable driving device for the propelling drive of the bale opener for providing a direct adaptation of fiber tuft output by changing the travelling speed of the bale opener. According to a further feature of the invention, the microcomputer control is connected with the drive for the height adjustment (feed) of the detaching device of the bale opener. During each pass, the detaching device remains at the same height for each bale group even if the apparatus according to the invention determines that the fiber material quantities are too large or too small. Only after completion of the pass is the vertical feed adjusted at the beginning of the consecutive pass. In case the apparatus according to the invention is connected with the bale opener which thus receives a signal whether or not a downstream-arranged machine processes fiber, information about a batch production and a real production may be obtained.

Particular advantages are achieved by positioning the apparatus at certain locations, by utilizing a plurality of light receivers and by utilizing a microcomputer for evaluation and control. By virtue of the apparatus according to the invention, the fiber material stream is correctly "measured" by ascertaining the actual outline (size) of the material. It is a further advantage that factors (for example, the air speed with which the fiber tufts are being forwarded) which significantly affect the material detection, may be taken into account with appropriate corrections.

BRIEF DESCRIPTION OF THE DRAWING

FIGS. 6a, 6b and 6c are schematic plan views of the preferred embodiment showing three different operational stages.

FIG. 7 is an axial sectional view of a duct portion illustrating the sensor unit installed therein according to a preferred embodiment.

FIG. 7a is a sectional view taken along line VIIa—VIIa of FIG. 7.

FIG. 8 is an axial sectional view of a duct portion, illustrating the sensor unit installed therein according to another preferred embodiment.

FIG. 8a is a sectional view taken along line VIIIa—VIIIa of FIG. 8.

DESCRIPTION OF THE PREFERRED EMBODIMENTS

Figure 1:
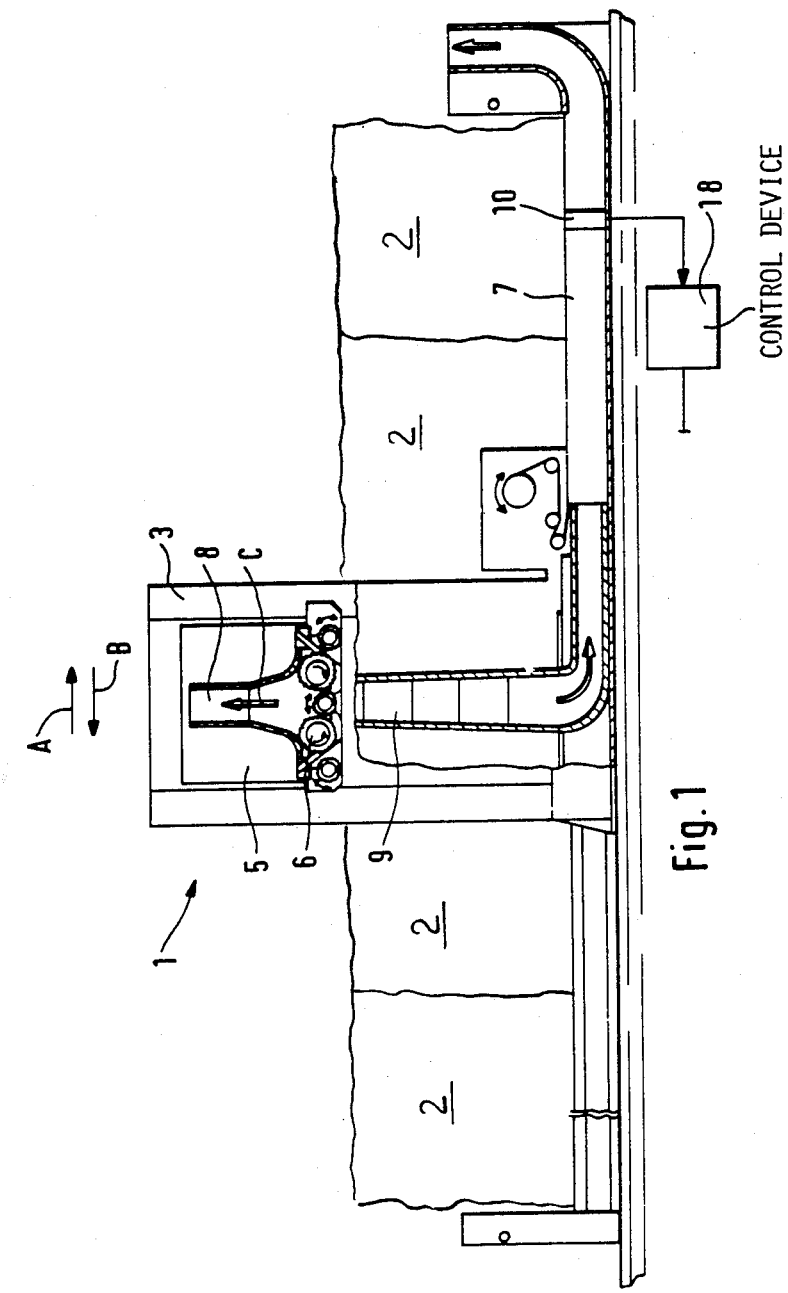
FIG. 1 is a schematic side elevational view of a fiber bale opener and a sensor unit, situated at a first location.

Turning to FIG. 1, there is schematically illustrated therein a bale opener 1 which may be, for example, a BLEN-DOMAT BDT model manufactured by Trützschler GmbH & Co. KG, Mönchengladbach, Federal Republic of Germany. The bale opener 1 serves for removing fiber tufts from the top of serially arranged, stationary fiber bales 2 supported on the floor. The bale opener 1 has a turret 3 which is supported for turning motion about a vertical axis on a truck 4 that may travel on ground-supported rails by means of wheels. The turret 3 has an outrigger housing 5 which accommodates a detacher 6. The outrigger housing 5 may, together with the detacher 6, be moved vertically relative to the turret 3. The detacher 6 is formed, for example, by a pair of sawtooth rollers for tearing (detaching) fiber tufts from the top surface of the bales 2 as the turret 3 travels along the bales. Underneath the turret 3, in the zone of the truck 4, there is supported a stationary, horizontally oriented suction channel 7 through which the detached fiber tufts pass. During operation, the truck 4, together with the turret 3, travels laterally along the free-standing fiber bales 2 back and forth as indicated by the arrows A and B, while the housing 5 and the detacher 6 travel above the bales 2. Above the detacher 6 there is arranged, in the outrigger housing 5, a suction duct 6 which is coupled to the stationary channel 7 by means of a duct portion 9a and a vertical telescoping duct 9 supported in and travelling with the turret 3. A blower (not shown) pneumatically connected to the duct series 9a, 9 and 7 generates an air stream which carries the fiber tufts through the duct series away from the detacher 6.

Figure 2:
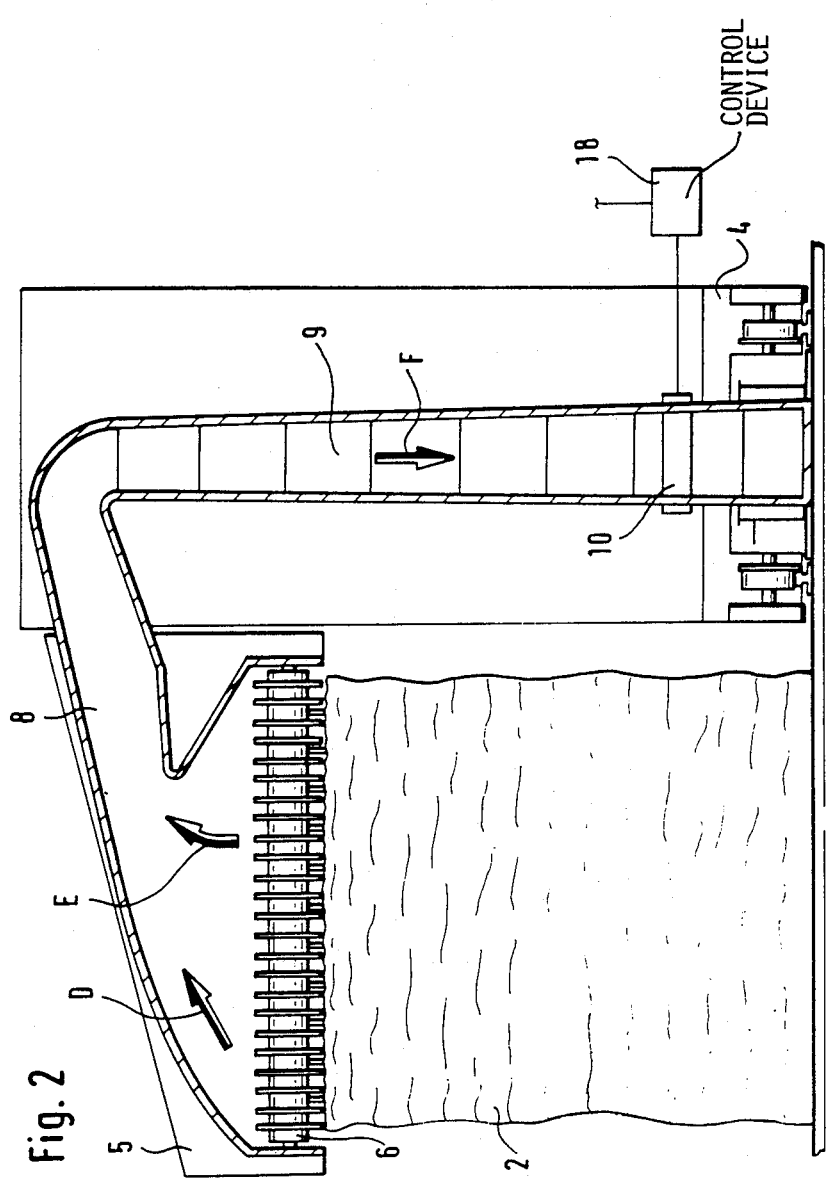
FIGS. 2 and 3 are enlarged schematic sectional elevational views of one part of the bale opener and a sensor unit, situated at a second and third location, respectively.
Figure 3:
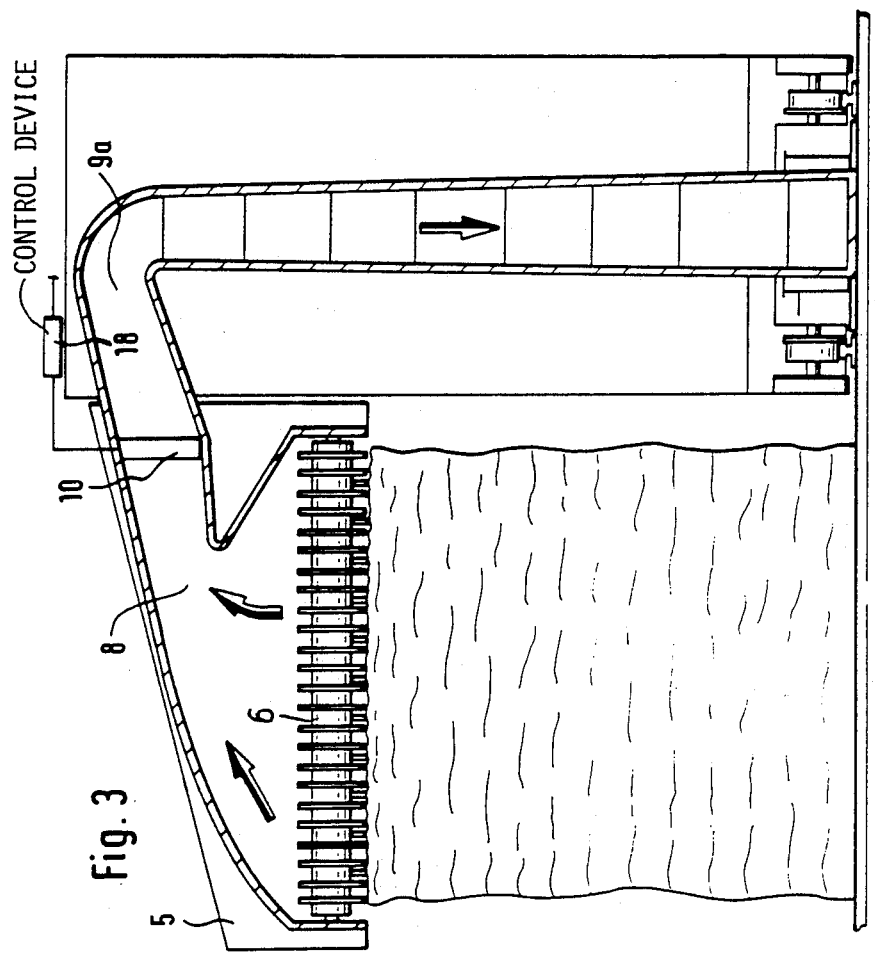

According to FIG. 1, a sensor unit 10 according to the invention is mounted in the stationary suction channel 7 and is electrically connected with an evaluating and control device 18. According to FIG. 2, the sensor unit 10 is arranged in the telescoping duct 9, whereas according to FIG. 3, the sensor unit 10 is situated in the suction duct portion 8, at the upstream end of the suction duct portion 9a.

Figure 4:
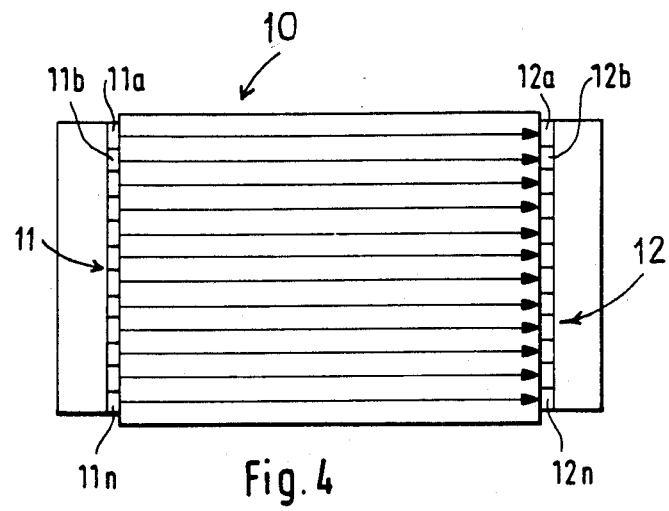
FIG. 4 is a schematic plan view of a preferred embodiment of the invention.

Turning to FIG. 4, the sensor unit 10 comprises a plurality of side-by-side arranged light emitters 11a, 11b ... 11n forming an emitter bank 11. Opposite the light emitters there is arranged a plurality of light detectors 12a, 12b ... 12n which, in turn, form a light detector bank 12. There may be provided, for example, 30 light emitters and 30 to 100 light detectors. The light beam extending from the light emitters to the light detectors is symbolized by parallel arrows.

Figure 5:
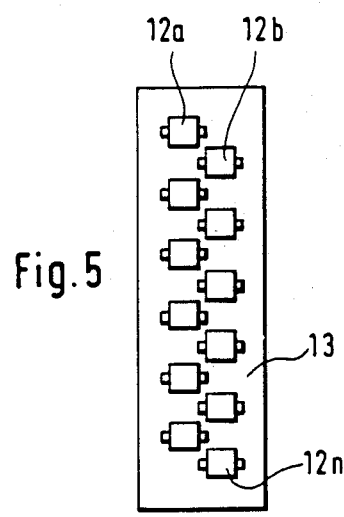
FIG. 5 is a schematic side elevational view of one part of the preferred embodiment of FIG. 4.

FIG. 5 illustrates a component carrier 13 on which there are arranged two rows of light detectors 12a to 12n (receiver diodes) such that the light detectors of one row are offset relative to those of the other row. The resolution depends upon the number of the rows.

FIG. 6a depicts a condition wherein between the light emitter bank 11 and the light detector bank 12 no fiber material is present so that all the light beams impinge on a light detector of the detector bank 12. FIG. 6b shows the presence of a small quantity of fiber material 14 (fiber tufts) between the emitter bank 11 and the detector bank 12, so that only one part of the light beams is prevented from reaching detectors of the detector bank 12. According to FIG. 6c, a large quantity (cluster) of fiber material 14 is present between the light emitter bank 11 and the detector bank 12, so that only a few light beams reach detectors of the detector bank 12. Thus, in the operational state depicted in FIGS. 6b and 6c, on the light detectors of the detector bank 12 a shadow appears whose area is an indication of the dimension and thus the quantity of the fiber material 14.

Turning now to FIGS. 7 and 7a, there is illustrated therein a conveying duct portion 15 in an axial and a radial sectional view, respectively. The wall 15a of the duct 15 may be sheet metal. The light emitter bank 11 and the light detector bank 12 are mounted in the duct such that their respective outer surface is flush with the inner wall face 15b of the duct wall 15a. By virtue of this arrangement, the fiber material, travelling in the direction as indicated with the arrow G, will encounter no obstruction.

Turning now to FIGS. 8 and 8a, there is shown therein a conveyor duct 15 on the inner walls 15b of which there is mounted the light emitter bank 11 and, opposite thereto, the light detector bank 12. At their upstream end, as viewed in the direction of fiber advance, there are provided oblique or rounded fiber tuft guide elements 16a and 16b and at the downstream end of the banks 11 and 12 there are arranged similar guide elements 17a and 17b. As seen in FIG. 8a, the sensor unit is formed of two emitter banks 11 and 11' arranged at 90° to one another and two detector banks 12 and 12', also arranged at 90° to one another, so that the four banks fully enclose the cross-sectional area of the flow passage. The guide elements 16a, 16, 17a and 17b substantially reduce obstructions to the material flow that would be caused by the inwardly protruding banks 11 and 12.

Figure 9:
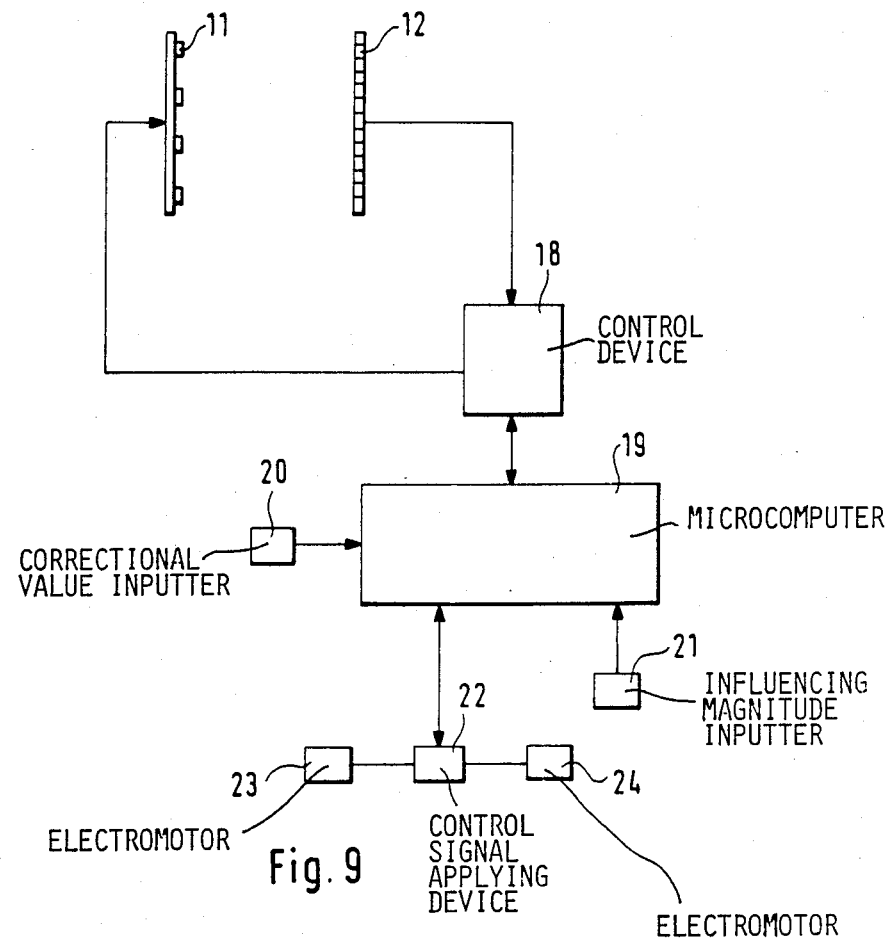
FIG. 9 is a block diagram showing an electronic circuitry connected with the sensor unit according to the invention.

Turning now to the block diagram illustrated in FIG. 9, the light emitter bank 11 and the light detector bank 12 are electrically connected with the emitter and detector control device 18 which, in turn, is connected to an electronic control device 19 which may be, for example, a TMS microcomputer manufactured by Trützschler GmbH & Co. KG. To the microcomputer 19 there are connected a device 20 for inputting correctional values (for example, type of material) and a device 21 for inputting information concerning additional influencing magnitudes, such as air speed. The control apparatus (microcomputer) 19 is electrically connected with a device 22 which, in order to apply control signals, is coupled with the drive 22 (electromotor) of the truck 4 and the drive 23 (electromotor) for the vertical adjustment (feed) of the detacher 6 of the bale opener 1.

It will be understood that the above description of the present invention is susceptible to various modifications, changes and adaptations, and the same are intended to be comprehended within the meaning and range of equivalents of the appended claims.

What is claimed is:

1. In an apparatus for determining quantities of textile fiber material during conveyance thereof by an air stream through a duct, including a sensor unit situated at the duct and arranged for monitoring the stream flowing through the duct and composed of a fiber/air mixture; the improvement wherein said sensor unit comprises a plurality of side-by-side situated light emitters forming an emitter bank and a plurality of side-by-side arranged light detectors forming a detector bank; said detector bank being situated spaced from and opposite to said emitter bank for providing a passage for the stream therebetween.

2. An apparatus as defined in claim 1, in combination with a duct portion of said duct; said duct portion having opposite inner wall faces; one of said inner wall faces carrying said emitter bank and another of said inner wall faces carrying said detector bank; said emitter bank being flush with said one inner wall face and said detector bank being flush with said other inner wall face.

3. An apparatus as defined in claim 1, wherein the emitter bank and the detector bank are each two in number and are arranged end-to-end at 90° to one another for enclosing a rectangular area through which the stream passes.

4. An apparatus as defined in claim 1, wherein said emitter bank and said detector bank are formed of infrared light emitters and infrared light detectors, respectively.

5. An apparatus as defined in claim 1, in combination with a duct portion of said duct; said duct portion having a rectangular, quadrilateral cross section; said sensor unit being mounted in said duct portion.

6. An apparatus as defined in claim 1, in combination with a duct portion of said duct; said duct portion having opposite inner wall faces; said emitter bank being mounted on one of said inner wall faces and protruding therefrom into said duct portion; said detector bank being mounted on another of said inner wall faces and protruding therefrom into said duct portion; said banks having respective upstream and downstream ends as viewed in a flow direction of the stream; further comprising fiber guiding means arranged at said upstream ends for smoothly guiding the stream over said banks.

7. An apparatus as defined in claim 6, further comprising additional fiber guiding means arranged at said downstream ends for smoothly guiding the stream off said banks.

8. An apparatus as defined in claim 1, further comprising evaluating means for forming an image of momentary fiber quantities situated between said emitter bank and said detector bank by determining the number and location of light detectors being simultaneously dark at a given time.

9. An apparatus as defined in claim 8, further comprising an emitter and detector control device connected to said light emitters and said light detectors and a microcomputer control apparatus connected to said evaluating device and said emitter and detector control device.

10. An apparatus as defined in claim 8, in combination with a fiber bale opener including a turret arranged for a back-and-forth travel alongside a series of floor-supported fiber bales to be opened, an outrigger housing mounted on the turret, a detacher accommodated in the outrigger housing and arranged for removing fiber tufts from top faces of the fiber bales; and suction conduit means for pneumatically removing the fiber tufts torn from the fiber bales from the detacher; said duct forming part of said suction conduit means.

11. The combination as defined in claim 10, wherein said suction conduit means comprises a stationary channel fixedly supported along a path of travel of said turret; said duct constituting said channel.

12. The combination as defined in claim 10, wherein said suction conduit means comprises a suction conduit part mounted in said turret and carried thereby; said duct constituting said suction conduit part.

13. The combination as defined in claim 10, wherein said suction conduit means comprises a suction conduit part situated in said outrigger housing; said duct constituting said suction conduit part.

14. The combination as defined in claim 10, wherein said suction conduit means comprises a stationary channel fixedly supported along a path of travel of said turret and a conduit portion situated downstream of said stationary channel as viewed in a direction of stream flow; said duct constituting said conduit portion.

15. The combination as defined in claim 10, wherein said fiber bale opener further comprises a variable-speed drive motor for propelling said turret; said apparatus further comprising an emitter and detector control device connected to said light emitters and said light detectors and a microcomputer control apparatus connected to said evaluating device, said emitter and detector control device and said variable-speed drive motor.

16. The combination as defined in claim 10, wherein said outrigger housing is mounted on said turret for vertical displacements with respect thereto; said fiber bale opener further comprising a drive motor for raising and lowering said outrigger housing; said apparatus further comprising an emitter and detector control device connected to said light emitters and said light detectors and a microcomputer control apparatus connected to said evaluating device, said emitter and detector control device and said drive motor.

* * * * *